United States Patent
Nagao et al.

(10) Patent No.: US 12,136,486 B2
(45) Date of Patent: Nov. 5, 2024

(54) MEDICAL INFORMATION PROCESSING DEVICE AND SYSTEM FOR PRIORITIZING ANALYSIS RESULT INFORMATION FOR A PATIENT

(71) Applicant: CANON MEDICAL SYSTEMS CORPORATION, Otawara (JP)

(72) Inventors: Takamasa Nagao, Saitama (JP); Muneyasu Kazuno, Nasushiobara (JP); Junya Suzuki, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 340 days.

(21) Appl. No.: 17/582,565

(22) Filed: Jan. 24, 2022

(65) Prior Publication Data
US 2022/0238207 A1 Jul. 28, 2022

(30) Foreign Application Priority Data
Jan. 26, 2021 (JP) .................. 2021-010379

(51) Int. Cl.
*G16H 30/40* (2018.01)
*G06T 7/00* (2017.01)
*G16H 10/60* (2018.01)
*G16H 30/20* (2018.01)

(52) U.S. Cl.
CPC ........... *G16H 30/40* (2018.01); *G06T 7/0012* (2013.01); *G16H 10/60* (2018.01); *G16H 30/20* (2018.01); *G06T 2207/10081* (2013.01); *G06T 2207/10088* (2013.01)

(58) Field of Classification Search
CPC ........ G16H 30/40; G16H 30/20; G16H 10/60; G06T 7/0012; G06T 2207/10081; G06T 2207/10088
See application file for complete search history.

(56) References Cited

U.S. PATENT DOCUMENTS

| | | | |
|---|---|---|---|
| 2011/0019882 A1* | 1/2011 | Iwase | G16H 30/20 |
| | | | 382/128 |
| 2018/0146941 A1 | 5/2018 | Sakaguchi | |
| 2019/0228524 A1* | 7/2019 | Chen | G16H 30/40 |
| 2022/0192581 A1* | 6/2022 | Maeda | A61B 5/0205 |

FOREIGN PATENT DOCUMENTS

| | | |
|---|---|---|
| JP | 2017-189237 A | 10/2017 |
| JP | 2018-89364 A | 6/2018 |
| JP | 2021-029387 A | 3/2021 |

OTHER PUBLICATIONS

Japanese Office Action dated Aug. 6, 2024, issued in Japanese Application No. 2021-010379.

* cited by examiner

*Primary Examiner* — Casey L Kretzer
(74) *Attorney, Agent, or Firm* — Oblon, McClelland, Maier & Neustadt, L.L.P.

(57) ABSTRACT

A medical information processing device according to an embodiment includes a processing circuitry. The processing circuitry is configured to acquire a plurality of sets of analysis result information on a plurality of analysis processes that are executed on at least one medical image obtained by capturing an image of a patient; sets, with respect to each disorder of the patient, a first priority that is a priority in displaying the acquired sets of analysis result information; and causes the sets of analysis result information to be displayed in an order corresponding to the first priorities that are set with respect to each disorder of the patient.

7 Claims, 4 Drawing Sheets

MEDICAL INFORMATION PROCESSING DEVICE AND SYSTEM FOR PRIORITIZING ANALYSIS RESULT INFORMATION FOR A PATIENT

CROSS-REFERENCE TO RELATED APPLICATIONS

This application is based upon and claims the benefit of priority from Japanese Patent Application No. 2021-010379, filed on Jan. 26, 2021; the entire contents of which are incorporated herein by reference.

FIELD

Embodiments described herein relate generally to a medical information processing device and a medical information processing system.

BACKGROUND

A problem to be solved by the embodiment disclosed herein and the accompanying drawings is to assist in radiographic interpretation of a result of analysis on a medical image. The problem to be solved by the embodiment of the disclosure and the accompanying drawings is not limited to the problem mentioned above. A problem corresponding to each effect achieved by each configuration presented by the embodiment described below can be positioned as another problem.

DETAILED DESCRIPTION

A medical information processing device and a medical information processing system according to an embodiment will be described below with reference to the accompanying drawings. In the following embodiment, components denoted with the same reference numerals perform the same operations and redundant description thereof will be omitted as appropriate.

First Embodiment

Figure 1:
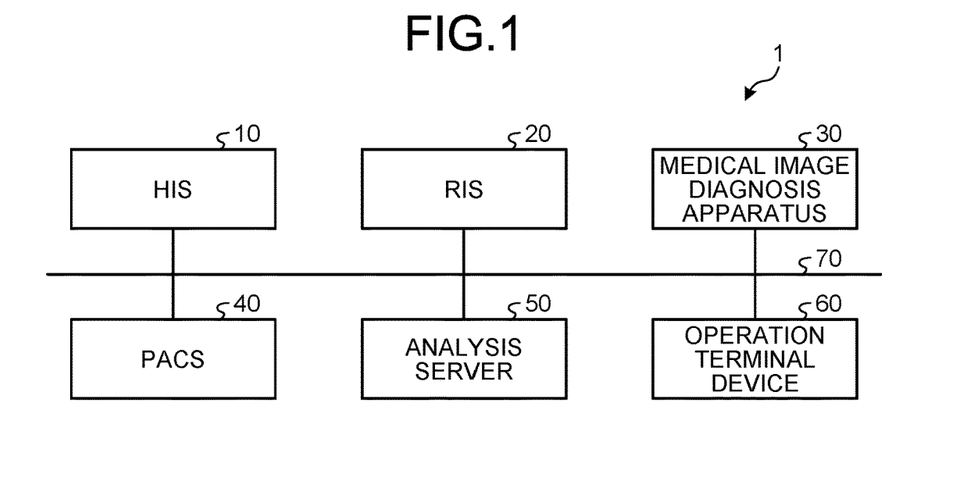
FIG. 1 is a block diagram illustrating an example of a configuration of a radiographic interpretation assist system according to a first embodiment.

FIG. 1 is a block diagram illustrating an example of a configuration of a radiographic interpretation assist system 1 according to a first embodiment. The radiographic interpretation assist system 1 includes a hospital information system (HIS) 10, a radiology information system (RIS) 20, a medical image diagnosis apparatus 30, a picture archiving and communication system (PACS) 40, an analysis server 50, and an operation terminal device 60. The radiographic interpretation assist system 1 is an example of a medical information processing system. The systems and the apparatuses are connected with one another such that they are able to communicate with each other via a network 70. The configuration illustrated in FIG. 1 is an example and the number of systems and apparatuses may be changed freely. An apparatus that is not illustrated in FIG. 1 may be connected to the network 70.

The HIS 10 manages various types of information on a subject, such as a patient. For example, the HIS 10 is implemented by a computer device, such as a server or a work station. More specifically, the HIS 10 stores electronic health record information that is a record of healthcare on the patient in a memory of the HIS 10, or the like. The electronic health record information contains diagnosis record information presenting a record of diagnoses on the patient made by healthcare professionals, such as a doctor, and examination information presenting results of blood examinations on the patient.

The RIS 20 manages various types of information. For example, the RIS 20 is implemented by a computer device, such as a server or a work station. More specifically, the RIS 20 stores examination order information that requests an examination by the medical image diagnosis apparatus 30 in a memory of the RIS 20, or the like. The examination order information contains object information, part information, and conduct urgency information. The object information is information presenting a purpose of conducting an examination. For example, in the object information, information presenting a disorder is set for the object of conducting the examination. The part information is information presenting a part of the patient on which the examination is to be conducted. The conduct urgency information is information indicating whether the examination should be carried out urgently.

The medical image diagnosis apparatus 30 is an apparatus that captures an image in order to examine the subject. For example, the medical image diagnosis apparatus 30 is an apparatus, such as an X-ray diagnosis apparatus, an X-ray computed tomography (CT) apparatus, a cardiovascular X-ray diagnosis apparatus (angiography), a magnetic resonance imaging apparatus, a nuclear medicine diagnosis apparatus or an ultrasonic diagnosis apparatus. On capturing a medical image, the medical image diagnosis apparatus 30 transmits medical image data to the PACS 40.

The PACS 40 is a server device that stores medical image data that is generated by the medical image diagnosis apparatus 30, etc. For example, the PACS 40 is implemented by a computer device, such as a server or a work station. On receiving the medical image data from the medical image diagnosis apparatus 30, the PACS 40 stores the medical image data in a memory of the PACS 40, or the like.

The analysis server 50 is a device that executes an analysis process on the medical image data. The analysis server 50 is an example of an analysis device. For example, the analysis server 50 is implemented by a computer device, such as a server or a work station. When the medical image data is stored in the PACS 40, the analysis server 50 executes a single or a plurality of analysis processes on the stored medical image data. In the analysis processes, any analysis may be performed. For example, the analysis process may be a process of detecting a disorder or a process of detecting a site of bleeding, a process of determining a blood flow state of the corresponding part, or another process. The analysis server 50 outputs a result of executing the analysis process.

The analysis result of the analysis process may be stored in a memory of the analysis server 50 or may be stored in a memory of another device, or the like.

The operation terminal device 60 is a terminal device that is operated by a healthcare professional, such as a doctor, who performs radiographic interpretation on the medical image data. The operation terminal device 60 causes results of analyses that are executed by the analysis server 50 to be displayed. The operation terminal device 60 is an example of a medical information processing device. The operation terminal device 60 is implemented by a computer device, such as a personal computer or a tablet.

The operation terminal device 60 displays a list of sets of medical image data stored in the PACS 40. The healthcare professional selects medical image data on which radiographic interpretation is to be performed from the list of sets of medical image data. The operation terminal device 60 acquires the analysis result of the analysis process that is executed by the analysis server 50 on the medical image data on the patient who is specified by the selected medical image data. In this case, the operation terminal device 60 acquires not only the result of analysis on the selected medical image data but also a result of analysis on another set of medical image data on the same patient. The operation terminal device 60 causes the single analysis result or a plurality of analysis results that are acquired to be displayed.

When a specific disorder or an injury is suspected, the healthcare professional conducts radiographic interpretation on the sets of medical data in an order corresponding to disorders or injuries. For example, when intracerebral hemorrhage is suspected, the healthcare professional finds a site of bleeding. The healthcare professional then checks the state of ischemia over the brain. The healthcare professional then checks the state of blood flow state over the brain. As described above, the healthcare professional conducts radiographic interpretation on the sets of medical image data in the order corresponding to the disorders and injuries, thereby diagnosing whether it is the corresponding disorder or injury. The same applies when checking the analysis results of the analysis processes. In other words, when a specific disorder or injury is suspected, the healthcare professional conducts a check on the analysis results in the order corresponding to the disorder or injury. The operation terminal device 60 thus displays the analysis results in the order in which the healthcare professional checks the analysis results.

The operation terminal device 60 will be described next.

Figure 2:
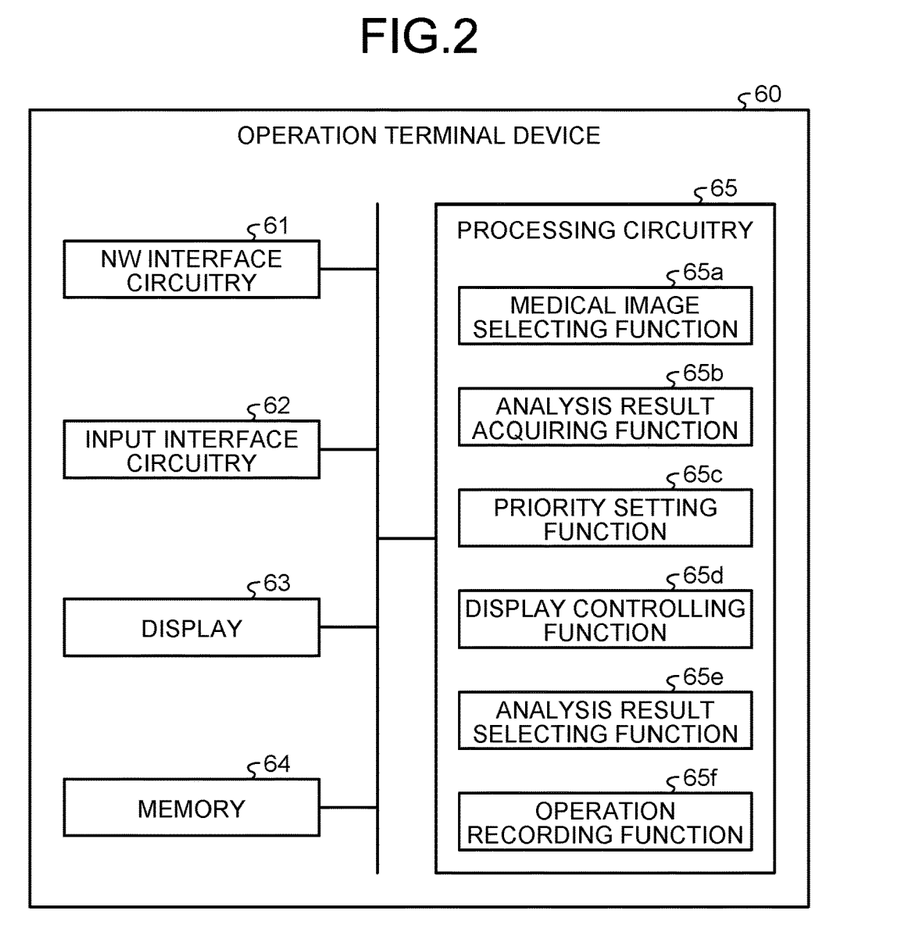
FIG. 2 is a block diagram illustrating an example of a configuration of an operation terminal device according to the first embodiment.

FIG. 2 is a block diagram illustrating an example of a configuration of the operation terminal device 60 according to the first embodiment. The operation terminal device 60 includes a network (NW) interface circuitry 61, an input interface circuitry 62, a display 63, a memory 64, and a processing circuitry 65.

The NW interface circuitry 61 is connected to the processing circuitry 65 and controls transmission and communication of various types of data that are conducted between the devices that are connected via the network 70. For example, the NW interface circuitry 61 is implemented by a network card, a network adapter, or a network interface controller (NIC), etc.

The input interface circuitry 62 is connected to the processing circuitry 65, converts an input operation that is received from an operator (healthcare professional) into an electric signal, and outputs the electric signal to the processing circuitry 65. Specifically, the input interface circuitry 62 converts an input signal that is received from the operator into an electric signal and outputs the electric signal to the processing circuitry 65. For example, the input interface circuitry 62 is implemented by a track ball, a switch button, a mouse, a keyboard, a touch pad with which an input operation is performed by touching an operation surface, a touch screen including a display screen and a touch pad that are integrated, a non-contact input circuitry using an optical sensor, and an audio input circuitry. Note that, in the description, the input interface circuitry 62 is not limited to those including physical operation parts, such as a keyboard. For example, an electric signal processing circuitry that receives an electric signal corresponding to an input operation from an external input device that is provided independently of the device and that outputs the electric signal to a control circuitry is also included in examples of the input interface circuitry 62.

The display 63 is connected to the processing circuitry 65 and displays various types of information and various types of image data that are output from the processing circuitry 65. For example, the display 63 is implemented by a liquid crystal display, a cathode ray tube (CRT) display, an organic EL display, a plasm display, or a touch panel.

The memory 64 is connected to the processing circuitry 65 and stores various types of data. The memory 64 stores various programs for implementing various functions by being read and executed by the processing circuitry 65. For example, the memory 64 is implemented by a semiconductor memory device, such as a random access memory (RAM) or a flash memory, a hard disk or an optical disk.

The processing circuitry 65 controls entire operations of the operation terminal device 60. The processing circuitry 65 includes, for example, a medical image selecting function 65a, an analysis result acquiring function 65b, a priority setting function 65c, a display controlling function 65d, an analysis result selecting function 65e, and an operation recording function 65f. In the embodiment, the respective processing functions implemented in the medical image selecting function 65a, the analysis result acquiring function 65b, the priority setting function 65c, the display controlling function 65d, the analysis result selecting function 65e, and the operation recording function 65f that are components are stored in the form of computer-executable programs in the memory 64. The processing circuitry 65 is a processor that reads the programs from the memory 64 and executes the programs, thereby implementing the functions corresponding to the respective programs. In other words, the processing circuitry 65 having read each of the programs has each of the functions illustrated in the processing circuitry 65 in FIG. 2.

FIG. 2 illustrates that the single processor implements the medical image selecting function 65a, the analysis result acquiring function 65b, the priority setting function 65c, the display controlling function 65d, the analysis result selecting function 65e, and the operation recording function 65f; however, a plurality of independent processors may be combined to configure the processing circuitry 65 and the respective processors may execute the programs, thereby implementing the functions. FIG. 2 also illustrates that the single memory, such as the memory 64, stores the programs corresponding to the respective processing functions; however, a plurality of memories may be arranged in a distributed manner and the processing circuitry 65 may be configured to read a corresponding program from an individual memory. The word "processor" used in the description given above refers to, for example, a central processing unit (CPU), a graphics processing unit (GPU), or a circuitry, such as an application specific integrated circuitry (ASIC), or a programmable logic device (for example, a simple programmable logic device (SPLD), a complex programmable logic device (CPLD) or a field programmable gate array (FPGA)). The processor reads the programs that are saved in the memory 64 and executes the programs, thereby implementing the functions. A configuration in which the programs are directly installed in the circuitry of the processor instead of saving the programs in the memory 64 may be employed. In this case, the processor reads the programs installed in the circuitry and executes the programs, thereby implementing the functions.

The medical image selecting function 65a selects medical image data from the list of sets of medical image data obtained by capturing images of the patient. More specifically, the medical image selecting function 65a receives an operation of selecting medical image data from a medical image list G10 (refer to FIG. 3) of a medical image list screen G1 including the list of sets of medical image data obtained by capturing images of the patient. In the embodiment, the operation terminal device 60 will be described, exemplifying the case where medical image data is selected from the list of sets of medical image data on the medical image list G10 of the medical image list screen G1. The operation terminal device 60 however only have to specify the patient by selecting medical image data. In other words, the operation terminal device 60 may select an analysis result not from the list of sets of analysis image data but from a list of analysis results.

The analysis result acquiring function 65b acquires a plurality of sets of analysis result information on a plurality of analysis processes executed on at least one set of medical image data obtained by capturing an image of the patient. The analysis result acquiring function 65b is an example of an acquisition unit. More specifically, the analysis result acquiring function 65b acquires the sets of analysis result information presenting the analysis results of the respective analysis processes that are executed on the medical image data on the patient that is specified by the medical image data that is selected by the medical image selecting function 65a. The analysis result information contains a thumbnail image, check urgency information, and result information. The thumbnail image is an image of a summary of the analysis result. The check urgency information is information presenting whether an urgent check is necessary. The result information is information presenting the analysis result.

More specifically, the analysis result acquiring function 65b specifies the patient corresponding to the medical image data that is selected by the medical image selecting function 65a. The analysis result acquiring function 65b acquires the analysis results of the analysis processes executed on the medical image data on the specified patient.

The priority setting function 65c sets analysis result priorities and disorder priorities. An analysis result priority is a priority of an analysis result to be displayed. In other words, the analysis result priorities are an order in which the analysis results are displayed. A disorder priority is a priority of a disorder to be displayed in the case where the analysis results are displayed with respect to each disorder. In other words, the disorder priorities are an order in which the disorders are displayed. The disorders with respect to the disorder priorities are not limited to diseases and may be injuries.

The priority setting function 65c sets, with respect to each disorder of the patient, analysis result priorities that are priorities in displaying the sets of analysis result information acquired by the analysis result acquiring function 65b. The priority setting function 65c is an example of a setting unit.

The analysis result priority is an example of first priorities. More specifically, the priority setting function 65c sets analysis result priorities that are an order in which the analysis results are displayed in an analysis result list image G100. The priority setting function 65c sets, with respect to each disorder of the patient, analysis result priorities of the sets of analysis result information.

For example, when priorities are set in advance with respect to the respective analysis processes, the priority setting function 65c sets an analysis result propriety with respect to each of the sets of analysis result information based on the setting information in which an analysis result priority is set with respect to each set of analysis result information.

Alternatively, in the case where analysis result priorities are set with respect to the respective analysis processes with respect to each disorder, the priority setting function 65c acquires information presenting a disorder of the patient from the electronic health record information or order information. Based on the analysis result priorities of the respective analysis processes associated with the acquired disorder, the priority setting function 65c sets analysis result priorities with respect to the respective sets of analysis result information.

The priority setting function 65c may set analysis result priorities based on an operation history. More specifically, the priority setting function 65c sets analysis result priorities based on operation history information in which an order in which operations of causing the sets of analysis result information to be displayed are received is recorded. In other words, the priority setting function 65c sets analysis result priorities based on the order of recording by the operation recording function 65f.

The priority setting function 65c may set analysis result priorities based on the number of detections corresponding to each of the sets of analysis result information. The number of detections is information presenting the number of detections based on the analysis result. What detected differs depending on the analysis process. For example, in the case of the analysis process of detecting a site of bleeding, the number of detections is the number of the detected sites of bleeding.

In the case where analysis result priorities are set based on the operation history or the number of detections, the priority setting function 65c may apply the priorities to all the sets of analysis result information or part of the sets of analysis result information. For example, in some cases, there are a plurality of sets of analysis processes on the same subject. In such a case, the priority setting function 65c may set analysis result priorities based on the operation history with respect to the sets of analysis result information on the same analysis process. An example will be described here. Assume that there are an analysis application from Company A that makes an analysis on intracerebral hemorrhage and an analysis application from Company B that makes an analysis on intracerebral hemorrhage. In this case, the priority setting function 65c sets analysis result priorities with respect to the analysis application from Company A and the analysis application from Company B based on the operation history.

Setting disorder priorities will be described next. The priority setting function 65c sets disorder priorities that are an order in which disorders are displayed in the analysis result list image G100 illustrated in FIG. 3.

The priority setting function 65c sets disorder priorities in displaying disorders of the patient. The disorder priorities are an example of second priorities. More specifically, the priority setting function 65c detects a disorder of the patient from the electronic health record information, the examination order information, and the analysis result information. The priority setting function 65c sets disorder priorities based on the electronic health record information presenting a healthcare record of the patient, the examination order information that requests acquisition of medical image data, and the analysis result information.

For example, when the names of disorders are on a healthcare record contained in the electronic healthcare record, the priority setting function 65c detects disorders presented by the healthcare record as disorders of the patient. When the examination result of a blood examination, or the like, contained in the electronic health record information indicates that the patient is suffering from a disorder, the priority setting function 65c detects the disorder presented by the examination result as a disorder of the patient. When the name of a disorder, or the like, is on the object information contained in the examination order information is in the object information contained in the examination order information, the priority setting function 65c detects the disorder presented by the object information as a disorder of the patient. When the analysis result information indicates that the patient is suffering from a disorder, the priority setting function 65c detects the disorder indicated by the analysis result information as a disorder of the patient. The priority setting function 65c thus sets disorder priorities with respect to the detected respective disorders based on the electronic health record information, the examination order information, and the analysis result information.

When the conduct urgency information contained in the examination order information indicates urgent conduction, the priority setting function 65c increases the disorder priority of the disorder presented by the object information contained in the examination order information. When it is presented that image diagnosis should be made urgently on the disorder in the diagnosis record information in the electronic health record information, the priority setting function 65c increases the disorder priority of the disorder in the diagnosis record information in the electronic health record information. Alternatively, when the check urgency information contained in the analysis result information indicates that a check should be made urgently, the priority setting function 65c increases the disorder priority of the disorder to be analyzed by the analysis process.

The healthcare professional, such as a doctor, makes an incorrect diagnosis in some cases. In other words, in some cases, the patient is suffering from a disorder different from the disorder presented by the diagnosis record information of the electronic health record information or the disorder presented by the object information of the examination order information. In such a case, examination information of the electronic health record information or the analysis result information present a disorder different from the disorder presented by the object information of the examination order information or the disorder presented by the object information of the examination order information. When an incorrect diagnosis would have been highly likely made, a check should be made on a disorder that is estimated as correct. When the disorder presented by the examination information of the electronic health record information or the analysis result information and the disorder presented by the diagnosis record information of the electronic health record information or the object information of the examination order information compete with each other, the priority setting function 65c increases the disorder priority of the disorder presented by the examination information of the electronic health record information or the analysis result information. In other words, the priority setting function 65c sets a disorder priority that differs with respect to each disorder according to reference information, such as the examination information of the electronic health record information, the analysis result information, the diagnosis record information of the electronic health record information, or the object information of the examination order information.

There is an effective analysis process on a specific disorder in some cases. In other words, appropriateness of the analysis process differs with respect to each disorder in some cases. Based on appropriateness information in which appropriateness values obtained by quantifying the degrees of appropriateness of the respective analysis processes are set with respect to each disorder, the priority setting function 65c sets analysis result priorities corresponding to the disorder with respect to the analysis result information. The priority setting function 65c thus is able to increase the analysis result priorities of the analysis result information that belongs to the specific disorder.

Figure 3:
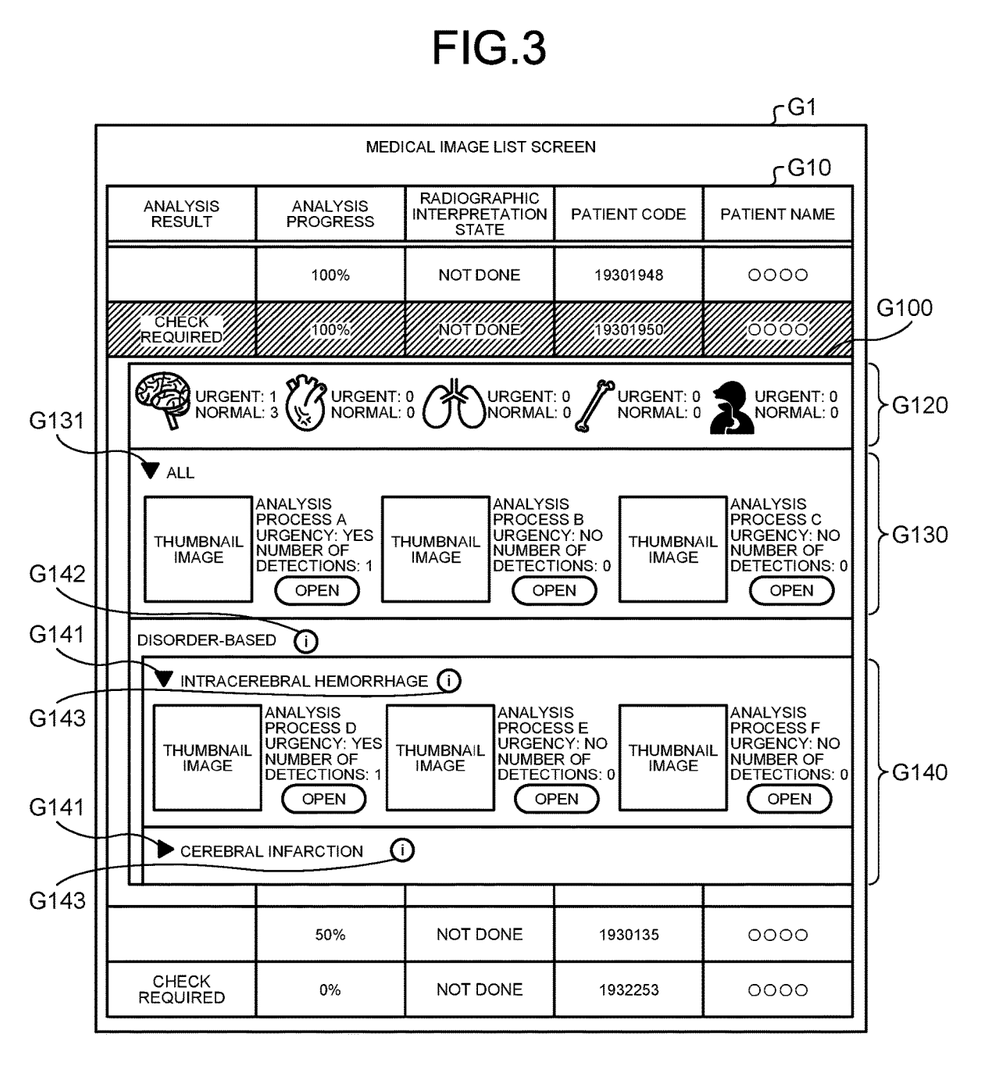
FIG. 3 is a diagram illustrating an example of a medical image list screen that is displayed by the operation terminal device according to the first embodiment.

The display controlling function 65d controls the display 63 to cause the display 63 to display various screens. For example, the display controlling function 65d causes the medical image list screen G1 to be displayed. FIG. 3 is a diagram illustrating an example of the medical image list screen G1 that is displayed by the operation terminal device 60 according to the first embodiment. The medical image list screen G1 includes the medical image list G10. The medical image list G10 is a list of the sets of medical image data stored in the PACS 40.

The display controlling function 65d causes the analysis result list image G100 to be displayed when medical image data is selected from the medical image list G10. Note that the medical image list screen G1 illustrated in FIG. 3 presents the state where the second medical image data is selected.

More specifically, the display controlling function 65d causes the analysis result list image G100 that is a list of analysis results on the medical image data on the patient corresponding to the selected medical image data to be displayed. The analysis result list image G100 includes a part-based display area G120, an all analysis results display area G130, and at least one disorder-based display area G140.

The part-based display area G120 is an area in which an overview of the results of analysis on the each part of the patient is displayed. In the part-based display area G120, each of the icons representing the respective parts is associated with the number of analysis results that should be checked urgently and the number of analysis results that should be checked in a normal order. The display controlling function 65d counts sets of check urgency information indicating that an urgent check should be made with respect to each part of the patient and thus causes the number of analysis results that should be checked urgently and the number of analysis results that should be checked in a normal order with respect to each part to be displayed.

The all analysis results display area G130 is an area in which all the analysis results that are collected by the analysis result acquiring function 65b are displayed. In other words, the all analysis results display area G130 is an area in which the analysis results collected by the analysis result acquiring function 65b are displayed without being sorted by disorders.

In the all analysis results display area G130, a thumbnail image, a check urgency display, the number of detections, and an open button are displayed with respect to each of the analysis results. The thumbnail image is an image representing the overview of an analysis result. The check urgency display is a display indicating whether it is necessary to make a check urgently. The number of detection is information presenting the number of detections based on the analysis result. What detected differs depending on the analysis process. For example, in the case of the analysis process of detecting a site of bleeding, the number of detections is the number of detected sites of bleeding. The open button is a button that receives an operation of causing the analysis result to be displayed.

The all analysis results display area G130 includes a first pull-down button G131. The first pull-down button G131 is a button that receives an operation on whether to display the analysis results in the all analysis results display area G130. The display controlling function 65d switches between displaying the analysis results and not-displaying the analysis results every time the first pull-down button G131 is pressed. The display controlling function 65d is capable of narrowing the display area by not displaying the analysis result.

The disorder-based display area G140 is an area in which analysis results are displayed with respect to each disorder. When the disorder-based display area G140 is displayed, the display controlling function 65d causes the disorders of the patient to be displayed in the order corresponding to the disorder priorities.

When displaying the analysis results in each disorder-based display area G140, the display controlling function 65d displays the sets of analysis result information in the order corresponding to the analysis result priorities that are set by the priority setting function 65c with respect to each disorder of the patient. The display controlling function 65d is an example of a display controller. In other words, the display controlling function 65d causes the sets of analysis result information in the order corresponding to the analysis result priorities that are set with respect to each disorder of the patient to be displayed. Accordingly, the display controlling function 65d displays each of the analysis results in the disorder-based display area G140.

As in the all analysis results display area G130, a thumbnail image, a check urgency display, the number of detections, and an open button are displayed with respect to each analysis result. The display controlling function 65d displays the analysis results contained in the disorder-based display area G140 in an order corresponding to the analysis result priorities that are set by the priority setting function 65c.

The disorder-based display area G140 includes a second pull-down button G141. The second pull-down button G141 is a button that receives an operation on whether to display the analysis results in the disorder-based display area G140. The display controlling function 65d switches between displaying the analysis results and not-displaying the analysis results every time the second pull-down button G141 is pushed. The display controlling function 65d is capable of narrowing the display area by not displaying the analysis results.

The display controlling function 65d causes a first notification button G142 and a second notification button G143 to be displayed. The first notification button G142 is a button for making a notification indicating the reason of the order in which the disorders are displayed in the disorder-based display area G140. When the first notification button G142 is pressed, the display controlling function 65d causes a screen presenting the reason why the priority setting function 65c sets the disorder priorities to be displayed. In other words, the display controlling function 65d displays the reason why the priority setting function 65c sets the disorder priorities. For example, when disorder priorities are set based on the analysis result information, the display controlling function 65d makes a display presenting that the priority is increased because it is determined that the patient is suffering from the disorder.

The second notification button G143 is a button for making a notification indicating the reason of the order in which the analysis results contained in the disorder-based display area G140 are displayed. When the second notification button G143 is pressed, the display controlling function 65d causes a screen presenting the reason why the priority setting function 65c sets the analysis result priorities to be displayed. In other words, the display controlling function 65d displays the reason why the priority setting function 65c sets the analysis result priorities. For example, the display controlling function 65d makes a display presenting that the order of displays is set based on the operation history or the order of displays is set based on the number of detections of analysis results. In this manner, the display controlling function 65d causes the reason why the priority setting function 65c sets the analysis result priorities or the disorder priorities to be displayed.

The analysis result selecting function 65e in FIG. 2 will be described. On the analysis result list image G100, the analysis result selecting function 65e receives an operation of selecting an analysis result. In other words, on the analysis result list image G100, the analysis result selecting function 65e receives an operation of causing an analysis result to be displayed.

The operation recording function 65f records the order in which operations of causing the respective sets of analysis result information to be displayed are received. The operation recording function 65f is an example of a recorder. More specifically, the operation recording function 65f records an order in which the analysis results that are received by the analysis result selecting function 65e are caused to be displayed. The operation history presenting the order in which the analysis results are caused to be displayed that is recorded by the operation recording function 65f is used by the priority setting function 65c to set analysis result priorities.

A screen display process that is executed by the operation terminal device 60 will be described.

Figure 4:
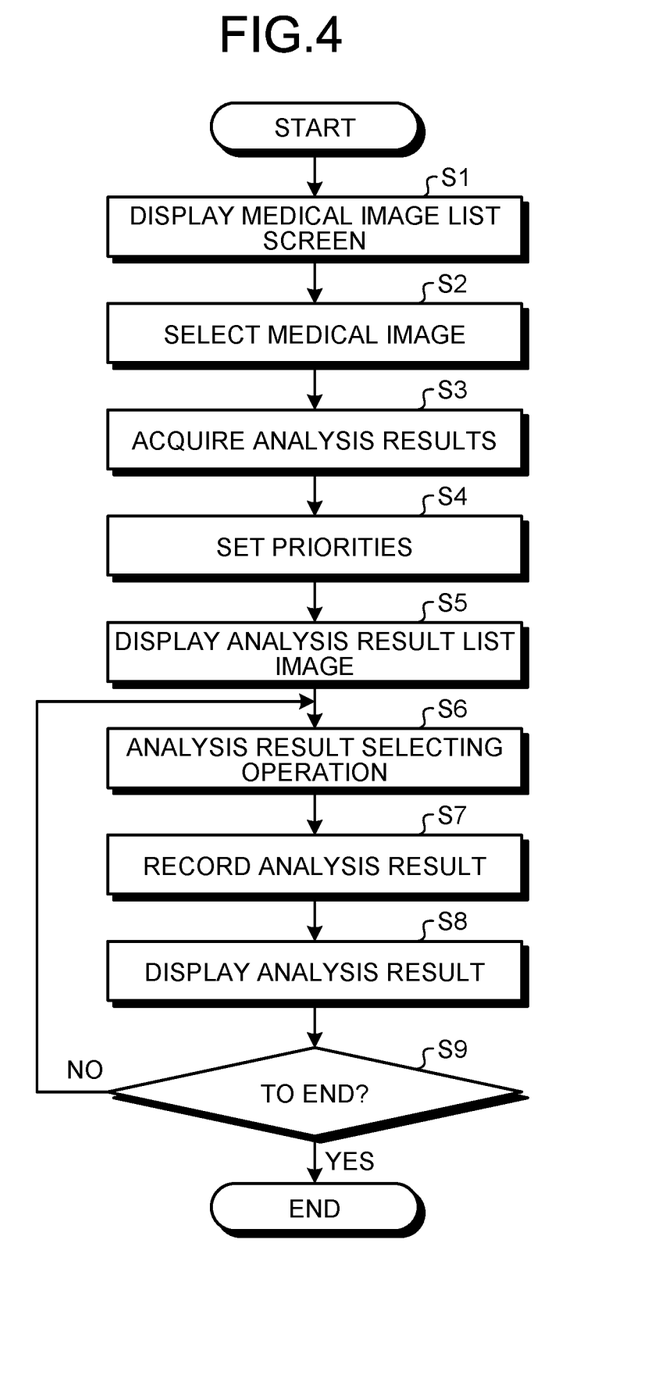
FIG. 4 is a flowchart illustrating an example of a screen display process that is executed by the operation terminal device according to the first embodiment.

FIG. 4 is a flowchart illustrating an example of the screen display process that is executed by the operation terminal device 60 according to the first embodiment.

The display controlling function 65d causes the medical image list screen G1 to be displayed (step S1).

The medical image selecting function 65a receives an operation of selecting medical image data from the analysis result list image G100 of the medical image list screen G1 (step S2).

The analysis result acquiring function 65b acquires results of analysis on a patient corresponding to the selected medical image data from the analysis server 50 (step S3).

The analysis result selecting function 65e sets a disorder priority with respect to each of disorders that are displayed in the analysis result list image G100 and sets an analysis result priority with respect to each of the analysis results (step S4).

The display controlling function 65d displays the analysis result list image G100 based on the disorder priorities and the analysis priorities that are set (step S5).

The analysis result selecting function 65e receives an operation of selecting an analysis result to be displayed from the analysis result list image G100 (step S6).

The operation recording function 65f records the analysis result that is specified by the operation that is received by the analysis result selecting function 65e (step S7).

The display controlling function 65d causes the analysis result, which is set, to be displayed (step S8).

The display controlling function 65d determines whether an operation of ending displaying the medical image list screen G1 is received (step S9). To continue displaying the medical image list screen G1 (NO at step S9), the operation terminal device 60 moves to step S6.

When an operation of ending displaying the medical image list screen G1 is received (YES at step S9), the operation terminal device 60 ends the screen display process.

As described above, the operation terminal device 60 according to the first embodiment acquires a plurality of sets of analysis result information on a plurality of analysis processes that are executed on at least one medical image. The operation terminal device 60 sets, with respect to each disorder of the patient, analysis result priorities that are priorities in displaying the acquired sets of analysis result information. The operation terminal device 60 then displays the sets of analysis result information in the order corresponding to the analysis result priorities that are set with respect to each disorder of the patient. Accordingly, the sets of analysis result information are arranged in the order in which a healthcare professional, such as a doctor, performs radiographic interpretation on the sets of analysis result information. The operation terminal device 60 thus enables assistance in radiographic interpretation on the medical image.

Modification 1

Figure 5:
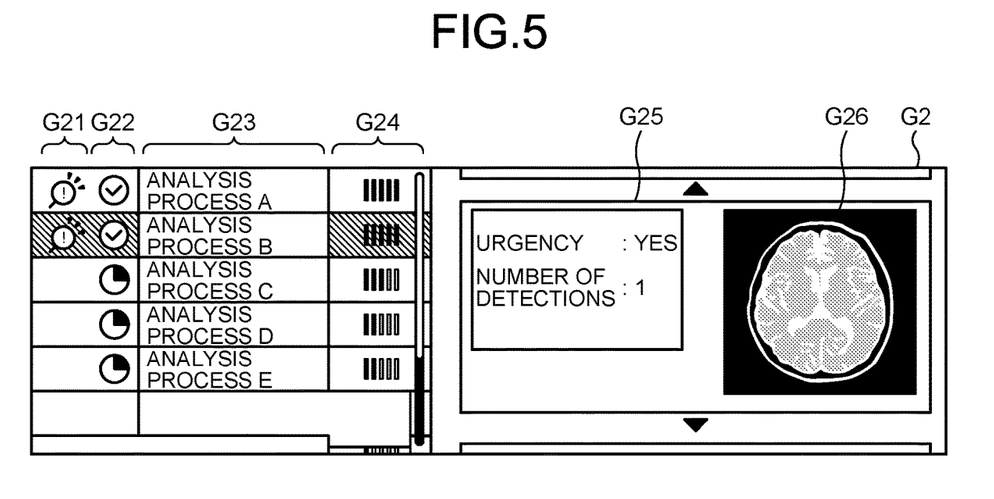
FIG. 5 is a diagram illustrating an example of a small analysis result list image that is displayed by an operation terminal device according to Modification 1.

In the first embodiment, the display controlling function 65d of the operation terminal device 60 causes the analysis result list image G100 illustrated in FIG. 3 to be displayed. In the operation terminal device 60, an increase of analysis processes increases analysis results to be displayed. When a large number of analysis results are displayed, the analysis result list image G100 becomes complicated in some cases. The display controlling function 65d may display a small analysis result list image G2 instead of the analysis result list image G100 illustrated in FIG. 3.

FIG. 5 is a diagram illustrating an example of the small analysis result list image G2 that is displayed by the operation terminal device 60 according to Modification 1. The small analysis result list image G2 is an image displaying a list of analysis results. The small analysis result list image G2 includes a check necessity display area G21, an analysis progress display area G22, an analysis process display area G23, a priority display area G24, and an overview display are G25.

The check necessity display area G21 is an area in which an icon indicating that it is necessary to check the analysis results is displayed. For example, in the check necessity display area G21, it is displayed that it is necessary to check the analysis result when an abnormality is contained in the analysis result. The analysis progress display area G22 is an area in which the rate of progress of the analysis process is displayed. The analysis process display area G23 is an area in which the analysis process of which analysis result is output is displayed. The priority display area G24 is an area in which an analysis priority is displayed. Each bar in the priority display area G24 serves as an icon for receiving an operation of displaying information on the reason why the analysis result priority is set. When a bar in the priority display area G24 is selected, the display controlling function 65d displays information on the reason why the analysis result priority is set. The overview display area G25 is an area in which the overview of the analysis result is displayed. The overview display area G25 has a thumbnail image G26 presenting the overview of the analysis result.

It has been described that the operation terminal device 60 includes the medical image selecting function 65a, the analysis result acquiring function 65b, the priority setting function 65c, the display controlling function 65d, the analysis result selecting function 65e, and the operation recording function 65f; however, not the operation terminal device 60 but another device may include all or part of these functions. For example, a computer device, such as a personal computer, a server, or a work station, may include these functions. These functions may be distributed to different devices or systems.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing device for prioritizing analysis result information for a patient, the medical processing device comprising:
    processing circuitry configured to
        receive a selection of a medical image data set from a medical image list containing a plurality of medical image data sets of patients,
        acquire a plurality of sets of analysis result information on a plurality of analysis processes that are executed on at least one medical image of a patient identified by the selected medical image data set,
        individually set second priorities of disorders of the patient to be displayed,
        individually set, with respect to the disorders of the patient, first priorities of the acquired sets of analysis result information to be displayed,
        display a disorder-based display area for each of the disorders of the patient on a display in an order of the second priorities, and
        display the sets of analysis result information in the disorder-based display area on the display in an order of the first priorities.

2. The medical information processing device according to claim 1, wherein the processing circuitry is configured to set the second priorities based on electronic health record information presenting a record of healthcare on the patient, examination order information requesting acquisition of the medical image, and the analysis result information.

3. The medical information processing device according to claim 1, wherein the processing circuitry is configured to, based on setting information containing the individually set first priorities of the plurality of analysis processes to the respective disorders, individually set the first priorities with respect to the sets of analysis result information.

4. The medical information processing device according to claim 1, wherein the processing circuitry is configured to record an order in which operations of causing the respective sets of analysis result information to be displayed are received and set the first priorities based on the recorded order.

5. The medical information processing device according to claim 1, wherein the processing circuitry is configured to set the first priorities based on a number of detections corresponding to each of the sets of analysis result information.

6. The medical information processing device according to claim 1, wherein the processing circuitry is configured to display individual reasons why the first priorities or the second priorities are set.

7. A medical information processing system for prioritizing analysis result information for a patient, the medical information processing system comprising:

an analysis device including processing circuitry configured to execute a plurality of analysis processes on a medical image of a patient; and a medical information processing device configured to cause information on results of analyses that are executed by the analysis device to be displayed, wherein the medical information processing device includes processing circuitry configured to receive a selection of a medical image data set from a medical image list containing a plurality of medical image data sets of patients, acquire a plurality of sets of analysis result information on a plurality of analysis processes that are executed on at least one medical image of a patient identified by the selected medical image data set, individually set second priorities of disorders of the patient to be displayed, individually set, with respect to the disorders of the patient, first priorities of the acquired sets of analysis result information to be displayed, display a disorder-based display area for each of the disorders of the patient on a display in an order of the second priorities, and display the sets of analysis result information in the disorder-based display area on the display in an order of the first priorities.

* * * * *